United States Patent [19]

White, Jr. et al.

[11] Patent Number: 5,338,537
[45] Date of Patent: Aug. 16, 1994

[54] ORAL COMPOSITIONS

[75] Inventors: Donald J. White, Jr., Fairfield; Edward R. Cox, Germantown; Rama Kasturi, Cincinnati, all of Ohio

[73] Assignee: The Procter & Gamble Company, Cincinnati, Ohio

[21] Appl. No.: 132,392

[22] Filed: Oct. 5, 1993

[51] Int. Cl.$^5$ .......................... A61K 7/16; A61K 7/18
[52] U.S. Cl. ...................................... 424/52; 424/49; 424/57
[58] Field of Search .................... 424/49–58

[56] References Cited

U.S. PATENT DOCUMENTS

| | | | |
|---|---|---|---|
| 3,105,798 | 10/1963 | Holliday et al. | 167/93 |
| 4,569,838 | 2/1986 | de Vries | 424/49 |
| 4,575,456 | 3/1986 | Hayes | 424/49 |
| 4,659,504 | 4/1987 | Hayes | 252/315.3 |
| 4,822,599 | 4/1989 | Mitra | 424/52 |
| 5,004,597 | 4/1991 | Majeti et al. | 424/52 |
| 5,094,842 | 3/1992 | Riley | 424/52 |
| 5,096,699 | 3/1992 | Gaffar et al. | 424/49 |
| 5,145,666 | 9/1992 | Lukacovic et al. | 424/52 |
| 5,188,820 | 2/1993 | Cummins et al. | 424/49 |
| 5,208,009 | 5/1993 | Gaffar et al. | 424/49 |
| 5,213,790 | 5/1993 | Lukacovic et al. | 424/52 |
| 5,258,173 | 11/1993 | Waterfield | 424/49 |
| 5,281,410 | 1/1994 | Lukacovic et al. | 424/52 |
| 5,281,411 | 1/1994 | Majeti et al. | 424/52 |
| 5,290,542 | 3/1994 | Liang | 424/52 |

FOREIGN PATENT DOCUMENTS

| | | |
|---|---|---|
| 341662 | 11/1989 | European Pat. Off. . |
| 0480811A2 | 4/1992 | European Pat. Off. . |
| 480811 | 4/1992 | European Pat. Off. . |
| 492998 | 7/1992 | European Pat. Off. . |
| 9200721 | 1/1992 | PCT Int'l Appl. . |
| 9400102 | 1/1994 | PCT Int'l Appl. . |

*Primary Examiner*—Shep K. Rose
*Attorney, Agent, or Firm*—Douglas C. Mohl; David K. Dabbiere; Jacobus C. Rasser

[57] ABSTRACT

Oral compositions providing antitartar and antigingivitis benefits containing an antitartar agent and a stannous salt.

6 Claims, No Drawings

ORAL COMPOSITIONS

TECHNICAL FIELD

The present invention relates to oral compositions which provide gum health benefits as well as an anti calculus benefit.

BACKGROUND OF THE INVENTION

Dental calculus is a deposit which forms on the surfaces of the teeth at the gingival margin. Supra gingival calculus appears principally in the areas near the orifices of the salivary ducts; e.g., on the lingual surfaces of the lower anterior teeth and on the buccal surfaces of the upper first and second molars, and on the distal surfaces of the posterior molars.

Mature calculus consists of an inorganic material which is largely calcium phosphate arranged in a hydroxyapatite crystal lattice structure similar to bone, enamel and dentine. An organic portion is also present and consists of desquamated epithelial cells, leukocytes, salivary sediment, food debris and various types of micro-organisms.

As the mature calculus develops, it becomes visibly white or yellowish in color unless stained or discolored by some extraneous agent. In addition to being unsightly and undesirable from an aesthetic standpoint, the mature calculus deposits may be sources of irritation of the gingiva.

A wide variety of chemical and biological agents have been suggested in the art to retard calculus formation or to remove calculus after it is formed. Mechanical removal of this material periodically by the dentist is, of course, routine dental office procedure.

The chemical approach to calculus inhibition generally involves crystal growth inhibition and/or chelation of calcium ion which prevents the calculus from forming and/or breaks down mature calculus by removing calcium.

Diphosphonates have been disclosed for use as anti calculus agents. U.S. Pat. Nos. 3,678,154, Jul. 18, 1972; 3,737,533, Jun. 5, 1973; and 3,941,772, Mar. 2, 1976 disclose such compounds.

Dental plaque comprises an accumulation of bacteria and bacterial byproducts on teeth. Plaque adheres tenaciously at points of irregularity or discontinuity such as on rough calculus surfaces, at the gum line and the like. A variety of approaches have been used to combat plaque including stabilized stannous fluoride as disclosed in U.S. Pat. No. 5,004,597 to Majeti et al.

The present inventors have now surprisingly found that stabilized stannous fluoride can be combined with a polyphosphonate to provide gum health benefits as well as less calculus and less stain.

It is an object of the present invention therefore to provide compositions which provide anti plaque and anti calculus benefits.

It is a further object of the present invention to provide products which provide anti plaque and anti calculus benefits with reduced stain.

It is still a further object of the present invention to provide products containing stabilized stannous fluoride and a polyphosphonate.

It is still a further object of the present invention to provide a preferred method of reducing plaque and calculus.

These and other objects will become clearer from the detailed description which follows.

All percentages and ratios used herein are by weight of the total composition unless otherwise specified. Additionally, all measurements are made at 25° C. in the composition or in an aqueous solution/dispersion unless otherwise specified.

SUMMARY OF THE INVENTION

The present invention embraces an oral composition comprising:
(a) a safe and effective amount of stannous fluoride;
(b) a safe and effective amount of stannous gluconate;
(c) a safe and effective amount of a polyphosphonate; and
(d) a pharmaceutically acceptable carrier.

The present invention also encompasses a method for retarding the development of plaque/gingivitis and calculus using these compositions.

DETAILED DESCRIPTION OF THE INVENTION

The compositions of the present invention comprise stannous fluoride, stannous gluconate, a phosphonate and a pharmaceutically acceptable carrier.

By "oral composition" as used herein means a product which in the ordinary course of usage is not intentionally swallowed for purposes of systemic administration of particular therapeutic agents, but is rather retained in the oral cavity for a time sufficient to contact substantially all of the dental surfaces and/or oral tissues for purposes of oral activity.

By "safe and effective amount" as used herein means sufficient amount of material to provide the desired benefit while being safe to the hard and soft tissues of the oral cavity.

By the term "comprising", as used herein, is meant that various additional components can be conjointly employed in the compositions of this invention as long as the listed materials perform their intended functions.

By the term "carrier", as used herein, is meant a suitable vehicle which is pharmaceutically acceptable and can be used to apply the present compositions in the oral cavity.

Stannous Fluoride

Stannous fluoride is the first essential component of the present compositions. This material is a staple item of commerce and is present in the present composition at a level of from about 0.05% to about 1.1%, preferably from about 0.4% to about 0.95%. It should be recognized that separate soluble stannous and fluoride salts may be used to form stannous fluoride in-situ as well as adding the salt directly. Suitable salts include stannous chloride and sodium fluoride among many others.

Stannous Gluconate

Stannous gluconate is the second of the essential components of the present compositions. This material is a known stannous chelate and may be provided to the present compositions as the chelate or as separate soluble stannous and gluconate salts and the chelate formed in-situ such as with stannous fluoride. Such salts include stannous chloride and sodium gluconate. Stannous gluconate is present in the present compositions at a level of from about 0.1% to about 11%, preferably from about 2% to about 4%.

Polyphosphonate

Azacycloalkane diphosphonates are diphosphonates suitable for use in the practice of this invention and are known in the literature and their synthesis forms no part of this invention. Reference can be made to U.S. Pat. No. 3,941,772, to Ploger et al., Mar. 2, 1976, incorporated herein by reference, for syntheses of these materials.

In general, azacycloalkane-2,2-diphosphonates have the formula

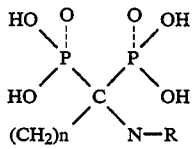

wherein R can be hydrogen or lower alkyl, e.g., methyl, ethyl, propyl, and the like, and n is an integer from 3 to 5. Such materials are prepared by reaction of the corresponding cyclic lactam with, for example, $H_3PO_3$. In this manner are prepared, for example, azacyclopentane-2,2-diphosphonic acid ("ACP"), N-methylazacyclopentane-2,2-diphosphonic acid ("NMAP") and azacycloheptane-2,2-diphosphonic acid, which is more properly named as 1-azacycloheptylidene-2,2-diphosphonic acid. Use of such materials as their acids or water-soluble salts, e.g., $Na+$, $K+$, $NH_4+$, salts, is contemplated by this invention. The sodium salts of 1,azacycloheptylidene-2,2-diphosphonic acid are referred to herein, collectively, as "AHP". (It will be appreciated that, as long as the salt is water soluble, the particular salt form used herein, i.e., mono-, di-, tri- or tetra-salt, is of no particular consequence in the practice of this invention, since it is the anion that provides the anti calculus benefit.) By "effective amount" of such diphosphonates herein is meant an amount sufficient to provide an anti calculus benefit.

Other polyphosphonates found useful in the present invention are those set forth in U.S. Pat. No. 3,488,419, to McCune et al., Jan. 6, 1970 incorporated herein in its entirety by reference. The polyphosphonates useful herein are selected from the group consisting of those of the formulae:

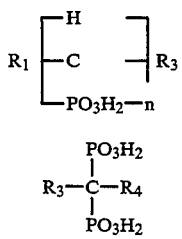

wherein $R_1$ and $R_2$ are hydrogen or $CH_2OH$; n is an integer of from 3 to 10; $R_3$ is hydrogen, alkyl containing from 1 to about 20 carbon atoms, alkenyl containing from 2 to about 20 carbon atoms, aryl (e.g., phenyl and naphthyl), phenylethenyl, benzyl, halogen (e.g., dimethylamino, diethyl amino, N-hydroxy-N-ethylamino, acetyl amino), $-CH_2COOH$, $-CH_2PO_3H_2$,

(OH) or $-CH_2CH(PO_3H_2)_2$; $R_4$ is hydrogen, alkyl of from 1 to 12 carbon atoms (e.g., methyl, ethyl, propyl, butyl, octyl and decyl), amino, benzyl, halogen (e.g., chlorine bromine and fluorine), hydroxyl, $-CH_2COOH$, $-CH_2PO_3H_2$, or $-CH_2CH_2PO_3H_2$; or a pharmaceutically acceptable salt thereof such as alkali metal (e.g., sodium and potassium), alkaline earth metal (e.g., calcium and magnesium), and ammonium or low molecular weight substituted ammonium (e.g., mono-, di, and triethanolammonium) salts, and a carrier suitable for use in the oral cavity, the pH of the composition being within the range from about 5.0 to about 11.0.

Operable polyphosphonates of the above Formula (I) include:

propane-1,2,3-triphosphonic acid;
butane-1,2,3,4-tetraphosphonic acid;
hexane-1,2,3,4,5,6-hexaphosphonic acid;
hexane-1-hydroxy-2,3,4,5,6-pentaphosphonic acid;
hexane-1,6-dihydroxy-2,3,4,5-tetraphosphonic acid;
pentane-1,2,3,4,5-pentaphosphonic acid;
heptane-1,2,3,4,5,6,7-heptaphosphonic acid;
octane-1,2,3,4,5,6,7,8-octaphosphonic acid;
nonane-1,2,3,4,5,6,7,8,9-nonaphosphonic acid;
decane-1,2,3,4,5,6,7,8,9, 10-decaphosphonic acid;

and the pharmaceutically acceptable salts of these acids, e.g., sodium, potassium, calcium, magnesium, ammonium, triethanolammonium, diethanolammonium, and monoethanolammonium salts.

Among the operable polyphosphonates encompassed by the above Formula (II) are ethane-1-hydroxy-1,1-diphosphonic acid;
methanediphosphonic acid;
methanehydroxydiphosphonic acid;
ethane-1,1,2-triphosphonic acid;
propane-1,1,3,3-tetraphosphonic acid;
ethane-2-phenyl-1,1-diphosphonic acid;
ethane-2-naphthyl-1,1-diphosphonic acid;
methanephenyldiphosphonic acid;
ethane-1-amino-1,1-diphosphonic acid;
methanedichlorodiphosphonic acid;
nonane-5,5-diphosphonic acid;
n-pentane-1,1-diphosphonic acid;
methanedifluorodiphosphonic acid;
methanedibromodiphosphonic acid;
propane-2,2-diphosphonic acid;
ethane-2-carboxy-1,
1-diphosphonic acid;
propane-1-hydroxy-1,1,3-triphosphonic acid;
ethane-2-hydroxy-1,1,2-triphosphonic acid;
propane-1,3-diphenyl-2,2-diphosphonic acid;
nonane-1,1 -diphosphonic acid;
decane-1-hydroxy-1,1-diphosphonic acid;
hexadecane-1,1-diphosphonic acid;
pent-4-ene-1-hydroxy-1,1-diphosphonic acid;
octadec-9-ene-1-hydroxy-1,1-diphosphonic acid;
3-phenyl-1,1-diphosphonoprop-2-ene;
octane-1,1-diphosphonic acid;
dodecane-1,1-diphosphonic acid;
phenylaminomethanediphosphonic acid;
naphthylaminomethanediphosphonic acid;
N,N-dimethylaminomethanediphosphonic acid;
N-(2-hydroxyethyl)-aminomethanediphosphonic acid;
N-acetylaminomethanediphosphonic acid;
aminomethanediphosphonic acid;
and the pharmaceutically acceptable salts of these acids, e.g., sodium, potassium, calcium, magnesium ammonium, triethanolammonium, diethanolammonium and monoethanolammonium salts. and the pharmaceutically acceptable salts of these acids, e.g., sodium, potassium, calcium, magnesium ammonium, triethanolammonium, diethanolammonium and monoethanolammonium salts.

Mixtures of any of the foregoing phosphonic acids and/or salts can be used in the compositions of this invention.

Ethane-1-hydroxy-1,1-diphosponic acid, an especially preferred polyphosphonate, has the molecular formula $CH_3C(OH)(PO_3H_2)_2$. (According to nomenclature by radicals, the acid might also be named 1-hydroxyethylidene diphosphonic acid). The most readily crystallizable salt of this acid is obtained when three of the acid hydrogens are replaced by sodium. Preferred salts for the purpose of this invention are the trisodium hydrogen salt which has the structure:

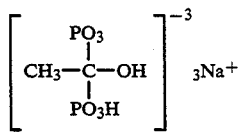

and the disodium salt.

The trisodium hydrogen salt normally crystallizes as the hexahydrate which loses some water during air-drying to yield a mixture of the hexa- and monohydrate averaging 3 to 4 molecules of water of hydration. The polyphosphonate is used as an effective amount generally from about 0.1 to about 6% preferably from about 0.5 to about 2.0%.

PHARMACEUTICALLY ACCEPTABLE CARRIER

The carrier for the components of the present compositions can be any vehicle suitable for use in the oral cavity. Such carriers include the usual components of mouthwashes, toothpastes, tooth powders, prophylaxis pastes, lozenges, gums and the like and are more fully described hereinafter. Dentifrices and mouthwashes are the preferred systems.

The abrasive polishing material contemplated for use in the present invention can be any material which does not excessively abrade dentin and do not provide calcium ions which may precipitate with, for example, the fluoride ions provided from stannous fluoride. These include, for example, silicas including gels and precipitates, insoluble sodium polymetaphosphate, β-phase calcium pyrophosphate, hydrated alumina, and resinous abrasive materials such as particulate condensation products of urea and formaldehyde, and others such as disclosed by Cooley et al. in U.S. Pat. No. 3,070,510, Dec. 25, 1962, incorporated herein by reference. Mixtures of abrasives may also be used. Abrasives such as calcium carbonate, calcium phosphate and regular calcium pyrophosphate are not preferred for use in the present compositions since they provide calcium ions which can complex F-.

Silica dental abrasives, of various types, can provide the unique benefits of exceptional dental cleaning and polishing performance without unduly abrading tooth enamel or dentin. Silica abrasive materials are also exceptionally compatible with sources of soluble fluoride. For these reasons they are preferred for use herein.

The silica abrasive polishing materials useful herein, as well as the other abrasives, generally have an average particle size ranging between about 0.1 and 30 microns, preferably 5 and 15 microns. The silica abrasive can be precipitated silica or silica gels such as the silica xerogels described in Pader et al., U.S. Pat. No. 3,538,230, issued Mar. 2, 1970 and DiGiulio, U.S. Pat. No. 3,862,307, Jun. 21, 1975 both incorporated herein by reference. Preferred are the silica xerogels marketed under the tradename "Syloid" by the W. R. Grace & Company, Davison Chemical Division. Preferred precipitated silica materials include those marketed by the J. M. Huber Corporation under the tradename, "Zeodent", particularly the silica carrying the designation "Zeodent 119". These silica abrasives are described in U.S. Pat. No. 4,340,583, Jul. 29, 1982, incorporated herein by reference.

The abrasive in the compositions described herein is present at a level of from about 6% to about 70%, preferably from about 15% to about 25% when the dentifrice is a toothpaste. Higher levels, as high as 95%, may be used if the composition is a toothpowder.

Flavoring agents can also be added to dentifrice compositions. Suitable flavoring agents include oil of wintergreen, oil of peppermint, oil of spearmint, oil of sassafras, and oil of close. Sweetening agents which can be used include aspartame, acesulfame, saccharin, dextrose, levulose and sodium cyclamate. Flavoring and sweetening agents are generally used in dentifrices at levels of from about 0.005% to about 2% by weight.

Dentifrice compositions can also contain emulsifying agents. Suitable emulsifying agents are those which are reasonably stable and foam throughout a wide pH range, including non-soap anionic, nonanionic, cationic, zwitterionic and amphoteric organic synthetic detergents. Many of these suitable surfactants are disclosed by Gieske et al. in U.S. Pat. No. 4,051,234, Sep. 27, 1977, incorporated herein by reference.

It is common to have an additional water-soluble fluoride compound present in dentifrices and other oral compositions in an amount sufficient to give a fluoride ion concentration in the composition at 25° C., and/or when it is used of from about 0.0025% to about 5.0% by weight, preferably from about 0.005% to about 2.0% by weight, to provide additional anticaries effectiveness. Preferred fluorides are sodium fluoride, indium fluoride, and sodium monofluorophosphate. Norris et al., U.S. Pat. No. 2,946,725, issued Jul. 26, 1960 and Widder et al., U.S. Pat. No. 3,678,154, issued Jul. 18, 1972 disclose such salts as well as others.

Water is also present in the toothpastes of this invention. Water employed in the preparation of commercially suitable toothpastes should preferably be deionized and free of organic impurities. Water generally comprises from about 10% to 50%, preferably from about 20% to 40%, by weight of the toothpaste compositions herein. These amounts of water include the free water which is added plus that which is introduced with other materials such as with sorbitol.

In preparing toothpastes, it is necessary to add some thickening material to provide a desirable consistency. Preferred thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as gum karaya, gum arabic, and gum tragacanth can also be used. Colloidal magnesium aluminum silicate or finely divided silica can be used as part of the thickening agent to further improve texture. Thickening agents in an amount from 0.5% to 5.0% by weight of the total composition can be used.

It is also desirable to include some humectant material in a toothpaste to keep it from hardening. Suitable humectants include glycerin, sorbitol, and other edible polyhydric alcohols at a level of from about 15% to about 70%.

Also desirable for inclusion in the toothpastes of the present invention are other stannous salts such as stannous pyrophosphate and antimicrobials such as quaternary ammonium salts, such as cetyl pyridinium chloride and tetradecylethyl pyridinium chloride, bis-biquanide salts, nonionic anti microbial salts and flavor oils. Such agents are disclosed in U.S. Pat. No. 2,946,725, Jul. 26,1960, to Norris et al. and U.S. Pat. No. 4,051,234, Sep. 27, 1977 to Gieske et al., incorporated herein by reference. Other optional components include peroxides, nitrate salts such as sodium and potassium, metal ions such as strontium zinc and indium. A suitable salt is a gluconate salt. These agents, if present, are included at levels of from about 0.01% to about 1.5%.

Another preferred embodiment of the present invention is a mouthwash composition. Conventional mouthwash composition components can comprise the carrier for the antimicrobial of the present invention. Mouthwashes generally comprise from about 20:1 to about 2:1 of a water/ethyl alcohol solution and preferably other ingredients such as flavor, sweeteners, humectants and sudsing agents such as those mentioned above for dentifrices. The humectants, such as glycerin and sorbitol give a moist feel to the mouth. Generally, on a weight basis the mouthwashes of the invention comprise 5% to 60% (preferably 10% to 20%) ethyl alcohol, 0% to 20% (preferably 5% to 20%) of a humectant, 0% to 2% (preferably 0.01% to 0.15%) emulsifying agent, 0% to 0.5% (preferably 0.005% to 0.06%) sweetening agent such as saccharin, 0% to 0.3% (preferably 0.03% to 0.3%) flavoring agent, and the balance water. The amount of additional antimicrobial agent in mouthwashes is typically from about 0.01% to about 1.5% by weight.

Suitable lozenge and chewing gum components are disclosed in U.S. Pat. No. 4,083,955, Apr. 11, 1978 to Grabenstetter et al., incorporated herein by reference.

The pH of the present compositions and/or its pH in the mouth can be any pH which is safe for the mouth's hard and soft tissues and will provide optimal effect of the stannous gluconate. Such pH's are from about 3.0 to about 5.0, preferably from about 4.0 to about 5.0, most preferably about 4.5.

METHOD OF MANUFACTURE

The carrier compositions of the present invention can be made using methods which are common in the oral products area. A specific method of manufacture is set forth in the Examples.

COMPOSITION USE

The present invention in its method aspect involves applying to the oral cavity safe and effective mounts of the compositions described herein. These amounts (e.g. from about 0.3 to about 15 g), if it is a toothpaste or mouthwash, are kept in the mouth for from about 15 to about 60 seconds.

The following examples further describe and demonstrate preferred embodiments within the scope of the present invention. The examples are given solely for illustration and are not to be construed as limitations of this invention as many variations thereof are possible without departing from the spirit and scope thereof.

EXAMPLES 1-4

Given below are dentifrice examples of the present invention.

|  | 1 | 2 | 3 | 4 |
|---|---|---|---|---|
| Sorbitol | 31.763 | 33.845 | 35.341 | 32.263 |
| Water-USP Purified | 18 | 18 | 18 | 18 |
| Stannous Fluoride | 0.454 | 0.454 | 0.454 | 0.454 |
| Saccharin | 0.455 | 0.455 | 0.455 | 0.455 |
| Sodium Gluconate | 8.328 | 6.246 | 4.164 | 8.328 |
| Stannous Chloride | 1.5 | 1.5 | 2.086 | 1.5 |
| AHP | 1.5 | 1.5 | 1.5 | 1 |
| Titanium Dioxide | 1 | 1 | 1 | 1 |
| Sodium Hydroxide | 0.75 | 0.75 | 0.75 | 0.75 |
| Silica | 20 | 20 | 20 | 20 |
| Synthetic sodium alkyl sulfate | 4 | 4 | 4 | 4 |
| Glycerin | 10 | 10 | 10 | 10 |
| Xanthan gum | 0.5 | 0.5 | 0.5 | 0.5 |
| Hydroxy ethyl cellulose | 0.75 | 0.75 | 0.75 | 0.75 |
| Flavor | 1 | 1 | 1 | 1 |

Option
1 SN++: Gluconate (1:4) + 1.5% AHP
2 SN++: Gluconate (1:3) + 1.5% AHP
3 SN++: Gluconate (1:1.54) + 1.5% AHP
4 SN++: Gluconate (1:4) + 1.0% AHP

What is claimed:

1. An oral anticalculus antiplaque/gingivitis composition with reduced tendency to stain consisting essentially of:
   (a) a safe and effective amount of stannous fluoride;
   (b) a safe and effective amount of stannous gluconate;
   (c) a safe and effective amount of polyphosphonate anion source having the following structure:

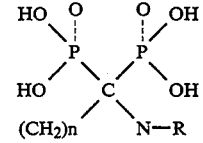

wherein R can be hydrogen or lower alkyl and n is an integer from 3 to 5
   (d) an acceptable oral dentrifice carrier.

2. An oral composition according to claim 1 in the form of a dentifrice wherein said polyphosphonate anion source is a salt of an azacycloalkane, 2,2-diphosphonate.

3. An oral composition according to claim 2 wherein said polyphosphonate anion source is a salt of 1-azacycloheptylidene-2,2-diphosphonate.

4. An oral composition according to claim 1 which consisting essentially of
   (a) from about 0.05 to about 1.1% stannous fluoride;
   (b) from about 0.15 to about 5.0% stannous chloride;
   (c) from about 0.4 to about 12% sodium gluconate
   (d) from about 0.1 to about 12% of a source of 1-azacycloheptylidene-2, 2-diphosphonate anions; and
   (e) an acceptable dentifrice oral carrier.

5. A method comprising contacting dental enamel surfaces with an effective amount of a composition according to claim 1 to reduce calculus and gingivitis.

6. A method comprising contacting dental enamel surfaces with an effective amount of a composition according to claim 4 to reduce calculus and gingivitis.

* * * * *